(12) United States Patent
Chornenky et al.

(10) Patent No.: US 11,712,576 B2
(45) Date of Patent: Aug. 1, 2023

(54) METHOD AND APPARATUS FOR CANCER TREATMENT

(71) Applicant: Minnesota Medical Physics LLC, Eden Prairie, MN (US)

(72) Inventors: Victor I. Chornenky, Minnetonka, MN (US); Ali Jaafar, Eden Prairie, MN (US)

(73) Assignee: Minnesota Medical Physics LLC, Eden Prairie, MN (US)

( * ) Notice: Subject to any disclaimer, the term of this patent is extended or adjusted under 35 U.S.C. 154(b) by 1093 days.

(21) Appl. No.: 16/366,495

(22) Filed: Mar. 27, 2019

(65) Prior Publication Data

US 2019/0299019 A1 Oct. 3, 2019

Related U.S. Application Data

(60) Provisional application No. 62/761,541, filed on Mar. 29, 2018.

(51) Int. Cl.
| | | |
|---|---|---|
| *A61N 2/02* | (2006.01) | |
| *A61N 1/36* | (2006.01) | |
| *A61N 2/00* | (2006.01) | |
| *A61N 1/40* | (2006.01) | |
| *A61K 31/00* | (2006.01) | |
| *A61N 1/32* | (2006.01) | |

(52) U.S. Cl.
CPC .......... *A61N 2/02* (2013.01); *A61N 1/36002* (2017.08); *A61N 1/40* (2013.01); *A61N 2/006* (2013.01); *A61K 31/00* (2013.01); *A61N 1/326* (2013.01); *A61N 1/3606* (2013.01); *A61N 1/36046* (2013.01)

(58) Field of Classification Search
CPC . A61N 2/006; A61N 2/02; A61N 1/40; A61N 1/3606; A61N 1/36002
See application file for complete search history.

(56) References Cited

U.S. PATENT DOCUMENTS

| | | | |
|---|---|---|---|
| 9,486,638 B2 | 11/2016 | Chornenky et al. | |
| 9,884,199 B2 | 2/2018 | Chornenky et al. | |
| 11,129,999 B2 | 9/2021 | Chornenky et al. | |
| 2007/0260107 A1* | 11/2007 | Mishelevich | A61N 2/004 600/14 |
| 2014/0357935 A1* | 12/2014 | Ilmoniemi | A61N 2/006 600/13 |

* cited by examiner

*Primary Examiner* — Christine H Matthews
(74) *Attorney, Agent, or Firm* — Skaar Ulbrich Macari, P.A.

(57) ABSTRACT

A method and apparatus for treatment of cancer is provided. The method can include systemic delivery of A3 selective adenosine receptor (A3AR) agonists CI-IB-MECA, cordycepin or similar drugs and providing simultaneous pulsed Electric Field (EF) stimulation to the treatment area. EF stimulation can be delivered in three orthogonal directions, which significantly increases expression of A3ARs on the cellular membranes and allows achieving a downstream apoptotic signal that is 4-6 fold stronger than the signal achieved with the agonist drugs alone.

7 Claims, 4 Drawing Sheets

METHOD AND APPARATUS FOR CANCER TREATMENT

PRIORITY

This application claims the priority benefit of U.S. Provisional Application No. 62/761,541, filed on Mar. 29, 2018, which is hereby incorporated herein by reference in its entirety.

FIELD

The invention relates to a method and apparatus for treatment of cancer, including brain cancer, using adenosine ligands and pulsed electric field (EF) stimulation. More specifically, it relates to enhancement of natural ability of the body to cause death to cancer cells through activation of A3AR apoptotic signaling pathways, particularly the pathway associated with P53 gene and WNT signaling pathway.

BACKGROUND

Cancer is a group of diseases involving abnormal cell growth with the potential to invade or spread to other parts of the body. Over 100 types of cancers affect humans. The most common types of cancer in males are lung cancer, prostate cancer, colorectal cancer and stomach cancer. In females, the most common types are breast cancer, colorectal cancer, lung cancer and cervical cancer. In the United States, more than 1.5 million cases of invasive cancer are diagnosed and more than 590,000 cancer related deaths happen each year. Under current estimates, two in five people will have cancer at some point in their lifetime. The financial cost of cancer is estimated to be more than $1.2 trillion USD per year.

There are three major methods of conventional cancer treatment: surgery, chemotherapy and radiation therapy.

Surgery is effective in removing early-stage tumors and is useful in debulking large tumors. The main disadvantage of surgical treatment is its inability to kill cancer cells dispersed around the edges of the primary tumor and in the multiple metastases that have spread across the body.

Radiation therapy is the use of ionizing radiation to kill cancer cells and shrink tumors. Ionizing radiation works by damaging the DNA of cancerous cells leading to their death. The disadvantages of radiation therapy include radiation damage to surrounding tissues, inability to kill all cancer cells in large tumors and existence of a limit for maximum delivered dose in one site that forbids using radiation therapy for recurrent treatments.

Chemotherapy is the use of anticancer drugs designed to slow or stop the growth of rapidly dividing cancer cells in the body. Surgery and radiation therapy remove or kill cancer cells locally in the targeted area, whereas chemotherapy works throughout the whole body and is able to kill both the prime and metastatic tumors. The major disadvantage of chemotherapy is its low selectivity to cancer cells, which leads to heavy damage to normal tissues that contain continuously dividing cells like skin, hairs, gut lining, etc.

Applying chemotherapy as a treatment for brain cancer faces a formidable obstacle presented by the blood-brain barrier (BBB). The BBB separates the patient's circulating blood from the microenvironment of their brain. The BBB is formed by endothelial cells of the capillary wall, astrocyte end-feet ensheathing the capillary, and pericytes embedded in the capillary basement membrane. This barrier system allows the passage of water, some gases, and lipid-soluble molecules by passive diffusion, as well as the selective transport of molecules such as glucose and amino acids that are crucial to brain function. The BBB serves a protective role; it prohibits penetration of harmful substances into the brain and protects specific brain homeostasis. At the same time, by hindering the entry of therapeutic compounds into the brain, the BBB presents a significant challenge for treatment of many brain diseases including brain cancer.

There have been numerous attempts to overcome the hindrance of drug delivery by the BBB that include physical disruption of the BBB, drug modification for easier passage across the BBB, and intrathecal injection of drugs into the brain. However, these approaches have suffered from shortcomings, including toxicity, decreased drug efficacy and invasiveness that can result in permanent brain damage.

A group researchers (A. J. Carman, et al.) recently working on improving delivery of therapeutic agents into the brain discovered that adenosine A1AR and A2aAR receptors are natural BBB modulators. They presented experimental in-vitro and animal studies that revealed the increase in BBB permeability is concentration dependent and allows large molecules (up to 70 KiloDalton) to pass through the BBB. The authors demonstrated that adenosine binds to its receptors (A1 or A2a) on BBB endothelial cells, the activation of which induces reorganization of actin cytoskeleton in BBB endothelial cells, resulting in tight junction disassembly and increasing paracellular cell permeability. The authors concluded that the adenosine-based control of the BBB has the potential for precise time-dependent and reversible modulation of the BBB for opening access of drugs to CNS.

The fundamental problem with this approach is that the high systemic concentration of adenosine-like drugs causes dilation of the whole capillary bed in the body and creates rapid blood pressure drop and disruption of normal blood circulation leading to life-threatening side effects. On the other hand, decreasing the systemic drug concentration to the tolerable levels will render the method inefficient.

There is a continuing need to modulate the BBB to facilitate the entry of therapeutic drugs into the CNS for treatment of neurological disorders including brain cancer.

Cancer is fundamentally a disease of tissue growth regulation. In order for a normal cell to transform into a cancer cell, the genes that regulate cell growth and differentiation must be altered.

The affected genes are divided into two broad categories. Oncogenes are genes that promote cell growth and reproduction. Tumor suppressor genes are genes that inhibit cell division and control their survival. Malignant transformation can occur through the formation of novel oncogenes, the inappropriate over-expression of normal oncogenes, or by the under-expression or disabling of tumor suppressor genes. Typically, changes in multiple genes are required to transform a normal cell into a cancer cell.

One of the most important cancer suppressor genes is P53—a gene that codes for p53 protein that regulates the cell cycle, DNA repair and cell apoptosis. P53 has been described as "the guardian of the genome", referring to its role in preventing genome mutations. The name of the gene comes from its product protein molecular mass: 53 KiloDalton. Discovery of the P53 gene was met by the medical community with great optimism and hopes for new effective methods of cancer treatment.

In normal cells the p53 protein level is low but DNA damage and other stressful intracellular events trigger an increase in its expression. The p53 protein has three major functions: growth arrest, DNA repair and apoptosis. The growth arrest stops the progression of the cell cycle, preventing replication of damaged DNA. During the growth arrest P53 activates the transcription of proteins involved in DNA repair. Apoptosis is the "last resort" to avoid proliferation of unrepairable cells that contain abnormal DNA.

The cellular concentration of the p53 protein is tightly regulated. While p53 can suppress unlimited proliferation, high levels of it may cause excessive apoptosis. The major regulator of p53 protein concentration is MDM2, which can trigger the degradation of p53 by the ubiquitin system.

In-vitro introduction of a normal P53 gene into P53-deficient cells has been shown to cause rapid death of cancer cells or arrest of further division. The P53 gene is well connected with multiple vital processes in the cell and its mutations can cripple the normal functioning of the cell. Mutations in the P53 gene can be seen in 50% of cancers; these mutations impair the anti-cancer effects of the gene and allow cancer cells to avoid apoptosis. Restoring the function of P53 would be a major step in curing many cancers. There is a hope that significant upregulation of under expressed or even damaged P53 still can lead to apoptosis. This is one of the major hypotheses for the development of new strategies for cancer treatment by activation of the P53 gene.

For a long time there has been a well-known observation that metastases from malignant tumors extremely rarely occur in muscle tissues. In an attempt to understand this phenomenon a group of Israeli scientists (Pnina Fishman et al.) discovered that migrating cancer cells in muscle tissues experience apoptosis via activation of adenosine receptor A3AR by extracellular adenosine, which is known to be expressed in muscles with higher (up to 3-fold) concentrations than in other tissues. Based on this discovery the group pioneered a new method of cancer treatment by activation of A3AR receptors with selective agonists. The group demonstrated that selective A3AR agonists IB-MECA and CI-IB-MECA cause reduction of metastases, migrating mobility of cancer cells and inhibition of proliferation in several cancers they experimented with: melanoma, colon, prostate carcinoma, lymphoma, pancreatic and hepatocellular carcinomas.

Further research demonstrated that A3ARs have significantly higher expression in cancer cells than in normal cells and that treatment with A3AR agonists mediates different effects on the pathological and normal cells. While specific A3AR agonists, such as CI-IB-MECA or CF101 induce apoptosis of cancer cells, normal cells are refractory to effects of the drugs. Similar data were reported by other authors in studies of the receptor expression levels in tumors derived from patients with colon, breast, small cell lung, pancreatic, hepatocellular carcinomas and melanoma in direct comparison with adjacent normal tissues. A direct correlation between A3AR expression levels and disease progression was described in several other studies. The more advanced cancer cells are, the higher the expression of A3ARs on their membranes. Increased expression of A3ARs indicates existence of a mechanism of the body that attempts to counteract uncontrolled proliferation and increase vulnerability of the cancer cells to apoptosis via A3AR receptor signaling.

Cancer cell metastasis requires the cell to acquire an early motile phenotype followed by transformation to an adhesive phenotype to facilitate interaction with the extracellular matrix proteins. This allows for dispersion of the malignant cells through the blood stream or lymph vessels to other parts of the body. A number of recent studies demonstrated that activation of A3AR receptors reduces the ability of cancer cells to migrate and metastasize. Also, inducing apoptosis by activation of A3ARs is especially efficient in metastatic cells because they have higher expression of A3ARs on their membranes.

Pnina Fishman et al. explained the anti-tumor activity of A3AR agonists via involvement of the WNT pathway in which A3AR signaling causes instability and deregulation that lead to tumor growth inhibition and apoptosis. WNT is an important pathway that regulates the proliferation of cells. WNT signaling is especially significant in early embryonic development and later during the growth and maintenance of various tissues.

A group of Japanese scientists (Tai-ichiro Otsuki et al.) demonstrated that extracellular adenosine via activation of A3AR agonist 2-CI-IB-MECA promotes P53-dependent apoptosis of lung cancer cells Lu-65. Apoptosis was observed in-vitro in a concentration dependent (0.01-10 mM) manner and was especially apparent at the highest concentrations in mM range, where 100% of cancer cells were destroyed in 48 hours. It appears that intense, acute activation of A3AR acts as a lethal input to the cancer cells. Similar results were obtained with A3AR agonist 2-CI-IB-MECA at concentration 100 µM. This important research suggests that A3AR regulates P53 transcription and causes apoptosis of cancer cells.

Independently from the Japanese scientists mentioned above, a group of Italian pharmacologists (Fabrizio Vincenzi et al.) demonstrated that the final destination of anticancer adenosine-A3AR signaling pathway in human glioblastoma U87MG cancer cells is gene P53, which inhibits proliferation and induces apoptosis. Normal cells of rat cortical neuron, which were used as a reference, were found to be refractory to A3AR activation. The conclusion of this study is that A3AR is functionally connected to the P53 gene and upon activation induces p53-dependent apoptosis of cancer cells. In full agreement with previous research it provides a convincing explanation of why apoptosis caused by activation of A3AR is so selective to cancer cells: P53 does not cause apoptosis of normal cells.

In the Italian in vitro studies A3AR agonist CI-IB-MECA (100 nM) was used alone or in combination with pulsed electromagnetic field (PEMF) stimulation. It should be noted that the pulsed electromagnetic field stimulation has two components—magnetic and electric field. Magnetic field easily penetrates into biological tissues but does not interact with cells and does not change any cellular functions. Magnetic field is created outside the body by a system of coils and serves only as a carrier of the electric field deep into tissues where it is generated by change in the magnetic field. This electric field significantly interacts with cells, in our case modifying expression of adenosine receptors A2aAR and A3AR on the cellular membranes. In a simple case of one-dimensional stimulation the number of these receptors increases approximately two times. It should be mentioned that the term PEMF used in literature is misleading and often wrongly implies that it is the magnetic field that is the active component of the PEMF stimulation. To avoid this ambiguity further in this disclosure we will use the term electric field (EF) stimulation or (EFS). In a series of experiments the Italian group demonstrated that activation of the P53 gene by A3AR was enhanced by EF stimulation, suggesting the synergistic role of A3AR agonist and EF stimulation in inhibiting proliferation and induction of apoptosis of cancer cells.

EFS in combination with synthetic agonists could be an innovative physiologic alternative to the drugs-only-approach. It should be noted that, contrary to the drug treatment, EFS mediates the tissue-specific agonist effects without desensitization and downregulation that are characteristic of interaction of high concentration of drugs with receptors. A decisive advantage of the combination of adenosine agonists with local EFS therapy is that it not only reduces the risk of adverse systemic effects, but also greatly increases the potency of anticancer adenosine agonist drugs.

Multiple in-vitro and animal studies suggest that there is an outstanding potential of A3AR-P53 and/or A3AR-WNT pathways for cancer treatment, but the practical methods of the effective treatment and adequate EFS instrumentation are still lacking.

One of the problems to be solved is the optimal drug concentration. Apoptosis of cancer cells is strongly concentration dependent. It has been demonstrated that 2-CI-IB-MECA concentration of 100 µM causes only a slowdown of tumor growth. It is clear that for successful curative treatment it would take significantly higher concentrations. The problem with high concentrations of A3AR agonists is that the A3AR receptor is expressed in many different tissues where it has a variety of vital functions. Thus, systemic delivery of drugs in very high concentration is likely to disrupt A3AR functions and cause dangerous side effects. The side effects can impose serious limitations on the level of acceptable concentrations that will render the treatment inefficient.

The Italian research suggests that the combination of A3AR agonists with exposure to EFS increases apoptosis of cancer cells and inhibits the tumor growth. It should be noticed though that the increase in apoptosis attributed to EFS over CI-IB-MECA alone was modest, only about 25-30%. These numbers look like a step in the right direction but are not good enough for curative treatment of cancer.

In the Italian experiments a simple pair of Helmholtz coils was used to provide EFS to cell cultures in Petri dishes. A new, significantly advanced EFS system should be developed for adequate stimulation of A3ARs in the clinical setting. To achieve curative treatment, a newly developed EFS system should be able to increase apoptosis at least in 4-5 times in comparison with the level induced by A3AR agonist alone.

The EFS system for clinical applications should be able to provide stimulation of A3ARs in tumors of different shapes and locations throughout the body. Also, the EFS system for cancer treatment must provide stimulation A3ARs across the tumor uniformly without missing any part of the tumor and its margin. It is important to mention that the PEMF system used by Italian scientists has a "dead zone" along the central axis of the Helmholtz coils where the stimulating electric field and the associated therapeutic effects are zero and close-to-zero around the axis of the coils. The "dead zone" in the treatment volume is inherent to one-coil or coaxial parallel coils stimulators such as Helmholtz coils. Helmholtz coils provide uniform magnetic field but the electric field, which is the active agent of the stimulation, is highly non-uniform and is changing across the treatment volume from maximum near the edges of the coils to zero at the central axis.

Another significant problem with using A3ARs in combination with EFS is that it activates not only A3ARs but also A2aARs. In several studies made by Italian scientists (Katia Varani et al.) it was established that EFS increases the concentration of A2aARs on cellular membranes that in the presence of free adenosine increases A2aARs-adenosine binding and leads to downregulation of the immune system. High concentration of free adenosine in tissue combined with EFS produces profound downregulation of the immune system.

Adenosine is present at elevated levels in cancer tumors due to increased intracellular adenosine production and release from the cancer cells. This is the result of oxygen deprivation and cellular ATP depletion. The extracellular concentrations of free adenosine could be up to 20-fold higher than those measured in surrounding normal tissue.

The high concentration of free adenosine found in tumors via A2aRs signaling decreases antitumor immunity and thus encourages tumor growth. A2AR has been recognized as an inhibitor of killer T-cell activation and effector function, and activity of activated natural killer (NK) cells. This is the reason why cancer cells evade destruction by the immune system in hypoxic, energy deprived tissues.

On the other hand, A3AR agonists activate NK cells that attack cancer cells causing their apoptosis. In the case of NK cells, the mechanism of apoptosis is different: it is initiated from outside the cell and the apoptotic signal is delivered to the cell via "death receptors" on the surface of the cellular membrane. This type of apoptosis is called extrinsic contrary to apoptosis that is initiated by signaling from inside the cell and called intrinsic.

Thus, there is a continuing need to develop efficient cancer therapies that can treat multiple forms of cancer including brain cancer.

SUMMARY

The main objective of the current invention is to provide a non-invasive method of treatment of cancer with little or no side effects, as well as an apparatus and system for delivering the treatment to the patient. Another objective can include providing a method of modulating BBB for the drug delivery into brain. Yet another objective can include inhibiting immunosuppressive activity of A2ARs. A further objective can be to provide a universal scanning electric field stimulation apparatus for treatment of tumors in different locations and metastases spread around the body.

To avoid immunosuppressive effects of activation of A2aARs, EFS of A3ARs for cancer treatment may be accompanied by blocking activity of A2aARs with systemic administration of selective A2aAR antagonists such as SCH-58261, TP455 or similar drugs. SCH-58261 is a drug which acts as a potent and selective antagonist for the adenosine receptor A2aAR, with more than 50-fold selectivity for A2aAR over the other adenosine receptors. So, for enhancing tumor immunotherapy and overall efficiency of the cancer treatment, instead of A3AR agonist alone, a "cocktail" of an A3AR agonist and an A2aAR antagonist may be used.

The novel method of treatment of cancer can be performed by combining systemic delivery of A3AR selective agonists CI-IB-MECA, cordycepin or similar drugs with EFS of the treatment area. In one preferred embodiment, EFS is delivered in three orthogonal directions, which significantly increases expression of A3ARs on the cellular membranes of cancer cells and allows achieving the downstream apoptotic signal that is 4-6 fold stronger than the signal achieved with A3AR agonists alone. A3ARs and the P53 gene are functionally connected; when the downstream A3ARs signal reaches the P53 gene, it activates production of the p53 protein which launches a biochemical sequence that causes apoptosis of cancer cells. Aside from the P53 gene, in some types of cancer, A3AR activation causes disruption of the WNT signaling pathway.

In case of treatment of brain tumors, in addition to A3AR agonists, one can provide simultaneous delivery of selective A2aAR agonist 2HE-NECA, ATL-146e, Lexiscan or the likes. Elevated systemic concentration of A2aARs agonist creates dilatation of blood vessels in the brain and, enhanced locally by strong EFS, opens the BBB for concomitantly delivered A3AR agonist. This method of opening the BBB is not limited to brain cancer but can be used for treatment of any other disease of the Central Nervous System (CNS) in general.

A several-fold increase in the apoptotic signal that is required for curative treatment of cancer is a challenging task. A simple rise of the amplitude of stimulating pulses will not be enough because there is a limit to the amplitude of electric pulses in tissues: above 30 mV/cm the electric field starts exciting nerves causing twitching of muscles. In this patent application a different approach to increasing A2aAR and A3AR signaling is suggested. It stems from the notion that adenosine receptors are tethered to the cytoskeleton and practically do not drift along the surface of the lipid membrane. Also, in solid tumors the cancer cells do not rotate and keep constant their angular position relative to the vector of applied electric field.

When an electric field is applied to a cell a transient process of about one microsecond duration is taking place. During this process the electric field is pushed out of the electrically conductive cytosol (Faraday cage effect) and is concentrated in the dielectric lipid membrane. In the part of the membrane orthogonal to the vector of the electric field it is amplified approximately 1000 times (ratio of the cell size and the thickness of the membrane) to a relatively high value of several V/cm, whereas at the "equator" of the cell where the membrane is parallel to the applied field, and normal to the membrane electric field is zero. It means that translocation of the A2aAR and A3AR receptors to the surface of the membrane happens only in the part of the membrane where electric field is strong and normal to the membrane. At the equator of the cell there is no normal to the membrane electric field and hence no translocation of the receptors takes place.

Because there is no drift along the membrane receptors, A2aAR and A3AR are translocated by the EF to the surface only in a small part of the membrane where the receptors become active and can bind with agonist drugs. In the rest of the membrane the receptors are not translocated and cannot bind with the agonist drugs and, because there is no drift to the area of the strong electric field they are never activated.

To translocate the receptors in the equator area to the membrane surface and make them active the stimulating electric field should be applied normally to the equatorial areas, for example, in two additional directions orthogonal to the membrane and to the vector of the first field. Additional switching polarity of the stimulating electric field allows doubling the number of active receptors on the cell. In short, to achieve a several-fold increase in numbers of A2aARs and A3ARs receptors on the membrane, the cells should be stimulated by a pulsed electric field in 3 orthogonal directions.

In this application three-dimensional EFS is achieved by arranging at least one coil on each of three planes that are orthogonal to each other. More than one coil can be provided on each plane. Also, on each of these three orthogonal planes, the coils are secured in such positions that the perpendiculars drawn from all three coils intersect in one point "O" where the stimulating EF of all three coils is at a maxima. Namely this maxima point is used during treatment by being applied to the tumors under computer control.

The apparatus in one example embodiment comprises EFS with three coils that are secured on orthogonal planes. During treatment the stimulator can be positioned adjacent the tumor stationary or can be preprogrammed to scan along the patient's body and deliver EFS to tumors of different shapes, sizes and locations.

The disclosed method of cancer treatment can include the systemic delivery of adenosine agonists of A3ARs in well-tolerated doses combined with local EFS that increases the potency of drugs at the tumor site. EFS increases expression of A3ARs on cellular membranes that causes a several-fold amplification of the downstream apoptotic signal that kills cancer cells.

The disclosed methods of treatment can be applied at any stage of the disease; it does not present the prohibitive detrimental side effects and can be applied to a patient multiple times without causing harmful long term side effects.

All existing devices for EFS are stationary. They also possess an inherent drawback: non-uniform stimulation of the target area with a "dead zone" in the middle of the stimulating field where the therapeutic electric field is below an effective minimum therapeutic value. For successful treatment of cancer an improved apparatus is described herein that will provide relatively uniform stimulation of different sizes and shapes of tumors without dead zones and with the therapeutic electric field above the effective minimum therapeutic value across the tumors.

A universal scanning apparatus for 3D EFS of tumors located in different parts of the body is also disclosed. This apparatus is computer controlled and allows treating tumors of any shape and location as well as metastases across the body.

The disclosure includes an EFS apparatus for treatment of cancer. The apparatus can include an applicator, comprising a first coil provided to the applicator, a second coil provided to the applicator, and a third coil provided to the applicator. Spatially, the three coils are arranged such that the planes of the coils are orthogonal to each other providing the opportunity to provide EF stimulation in three orthogonal planes. Further, the first, second and third coils can be arranged in the applicator such that a straight line drawn perpendicular from each coil defines an intersection of the lines vertically below the applicator at a point where a stimulating electrical field for each of the first, second and third coils is at a maximum value.

The applicator can be shaped as a triangular pyramid, and each of the first, second and third coils can be disposed on a separate plane of the triangular pyramid.

Each of the first, second and third coils can be single coils or multi-wind coils, such as double coils.

A first actuator can be coupled to the applicator to articulate the applicator in a first axis. A second actuator can be coupled to the applicator to articulate the applicator in a second axis. A third actuator can be coupled to the applicator to articulate the applicator in a rotational axis. The second axis can be perpendicular to the first axis.

A computer can be coupled to the applicator and configured to control the movement of the applicator during a treatment regimen. The computer can be configured to control the energizing of each of the first, second and third coils of the applicator during a treatment regimen.

The disclosure further includes a method of treating a cancerous tumor in a patient. The method can include providing EFS to the tumor to increase the expression of A3ARs on a surface of cancer cells of the tumor and delivering a dose of A3AR agonist to the patient to induce apoptosis of the cancer cells of the tumor.

The step of providing EFS to the tumor can include arranging a first coil, a second coil and a third coil in an applicator such that a straight line drawn perpendicular from each coil defines an intersection of the lines vertically below the applicator at a point where a stimulating electrical field for each of the first, second and third coils is at a maximum value. The applicator can be configured as a triangular pyramid, and each of the first, second and third coils can be disposed on a separate plane of the triangular pyramid.

The EF stimulation can be applied simultaneously with A3AR agonist delivery. The A3AR agonist can be CF101.

A dose of A2aAR agonist can be delivered to the patent to cause permeation of the blood-brain barrier. Delivered systemically in well tolerated doses, A2aAR agonist combined with EF stimulation of the brain opens the BBB in a controllable way. The degree of openness of BBB can be controlled by the intensity of EFS which can be selected to fit the size of drug molecule selected for treatment. The method of opening BBB using combination of A2AR agonists and EF stimulation of the brain can be used not only for the cancer treatment as disclosed in the patent application but also for treatment of different CNS diseases such as Alzheimer disease, Parkinson disease, multiple sclerosis etc.

The A3AR agonist can be cordycepin and can be delivered simultaneously with the A2AR agonist.

The disclosure still further includes a method of inducing apoptosis of cancer cells of a tumor in the brain of a patient. The method can include delivering a dose of A2aAR agonist to the patent to cause permeation of the blood-brain barrier, providing EFS to the tumor to increase the expression of A3ARs on a surface of cancer cells of the tumor, and delivering a dose of A3AR agonist to the patient that reaches the tumor in the brain via the permeated blood-brain barrier.

The dose of A2aAR agonist and the dose of A3AR agonist can be delivered to the patient simultaneously.

The step of providing EFS to the tumor can include arranging a first coil, a second coil and a third coil in an applicator such that the coils are secured on three mutually orthogonal planes and a straight line drawn perpendicular from each coil defines an intersection of the lines vertically below the applicator at a point where a stimulating electrical field for each of the first, second and third coils is at a maximum value.

The disclosure additionally includes a method of opening a patient's blood-brain barrier to their brain. The method can include delivering a systemic dose of A2aAR agonist to the patient and providing pulsed electric field stimulation (EFS) to the brain of the patient. The EFS can be one-dimensional, two-dimensional or three-dimensional.

The disclosure also includes a method of inducing apoptosis of cancer cells of a tumor in the brain of a patient. The method can include delivering a systemic dose of A2aAR agonist to the patent, providing electric field stimulation to the brain to simultaneously increase the expression of A2aARs on the cells responsible for blood-brain barrier permeation and the expression of A3ARs on the surface of cancer cells of the tumor, and delivering a systemic dose of A3AR agonist to the patient that reaches the tumor in the brain via the permeated blood-brain barrier.

The dose of A2aAR agonist and the dose of A3AR agonist can be delivered to the patient simultaneously. The A3AR agonist can be cordycepin.

The step of providing PEMF stimulation to the tumor can include arranging a first coil, a second coil and a third coil in an applicator such that a straight line drawn perpendicular from each coil defines an intersection of the lines vertically below the applicator at a point where a stimulating electrical field for each of the first, second and third coils is at a maximum value.

The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

Figure 1:
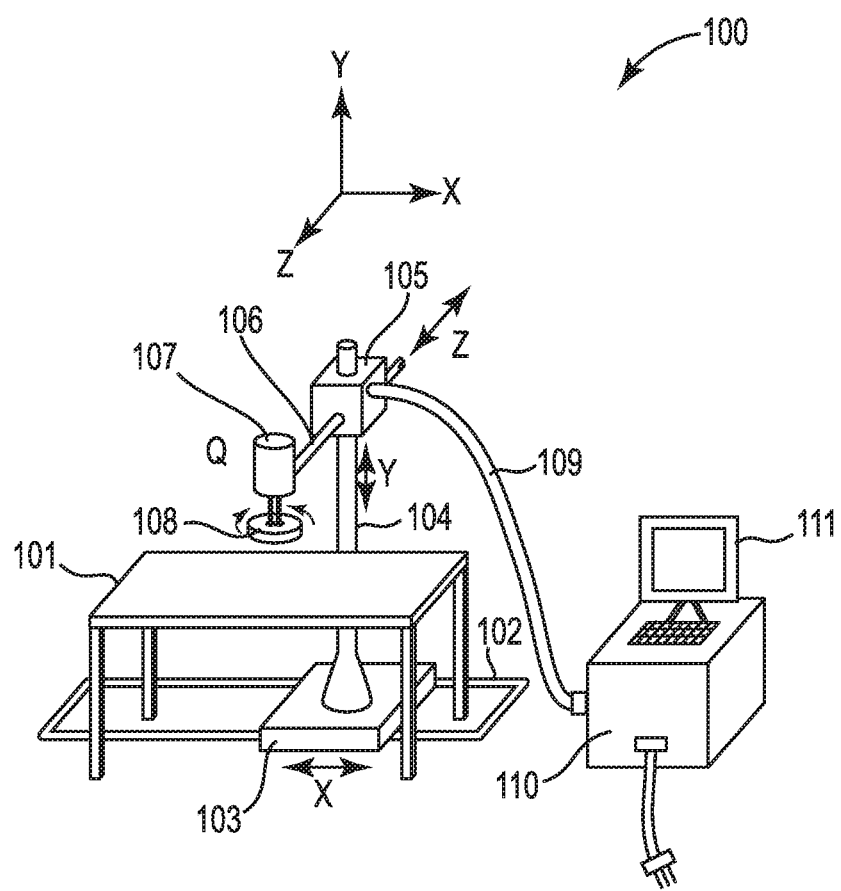
FIG. 1 is a schematic representation of scanning EFS apparatus with 3D stimulation capabilities.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the scope of the invention as defined by the appended claims.

DETAILED DESCRIPTION

In the following descriptions, the present invention will be explained with reference to various example embodiments; nevertheless, these example embodiments are not intended to limit the present invention to any specific example, embodiment, environment, application, or particular implementation described herein. Therefore, descriptions of these example embodiments are only provided for purpose of illustration rather than to limit the present invention.

A universal scanning EFS apparatus 100 for treatment of different locations of tumors is depicted in FIG. 1. A table 101 is also provided for positioning a patient in horizontal position for treatment with apparatus 100. A horizontal rack 102 is provided on which a first actuator 103 slides along the table 101 (axis X). A vertical shaft 104 is coupled to a first actuator 103 and connected to a second actuator 105. The second actuator 105 can slide along shaft 104 in the vertical direction (axis Y). A horizontal shaft 106 is slidably coupled to the second actuator 105 and is movable in horizontal direction along axis Z. A third actuator 107 is secured at the end of shaft 106. Third actuator 107 provides rotational motion around axis Y (angle ϑ) of EF stimulator 108 (also referred to herein as the stimulator, PEMF applicator or applicator).

A set of coils are secured on the PEMF applicator 108. Actuators 103, 105, 107 and EF stimulator 108 are coupled via multi conductor cable 109 to electronics block 110. The electronic block 110 includes a power supply and a programmable controller that places the stimulator 108 in a position with coordinates X, Y, Z, ϑ and controls durations of stimulation in each dwelling position. A computer 111 is provided and is used for preprogramming of the treatment plan and execution of that plan during treatment. A power cable 112 for powering the whole apparatus is connected to a wall power outlet.

The described apparatus 100 is exemplary of one embodiment. Other computer-controlled mechanical systems can be provided for positioning of the stimulator 108 in a sequence of predetermined dwelling positions and dwelling times in further embodiments.

A second stimulator having a similar configuration to the first can also be provided below the table 101 so that treatment can be provided to the patient from two opposing sides simultaneously. The second stimulator can be controlled by a computer just like the first stimulator.

Figure 2A:
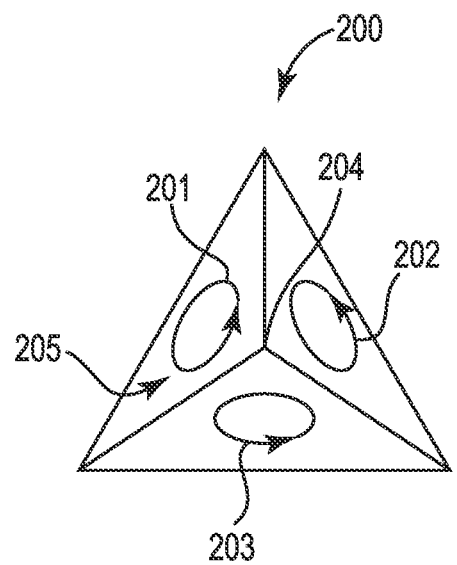
FIGS. 2A-2D are schematic illustrations of the positioning electromagnetic coils on the 3D PEMF stimulator.

FIGS. 2A-2D schematically illustrate different implementations of the set of coils in the EF stimulator 200. In FIG. 2A, coils 201, 202 and 203 are secured on the side planes of a symmetric pyramid with apex 204 and horizontal base 205. The angles between side planes of the pyramid are close to 90 degrees.

Each of the three coils 201, 202 and 203 are activated sequentially with short delays in time. Switching directions of the currents in coils, rotational motion around vertical axis Y (angle ε) and translational motions along axes X, Y, Z brings stimulator 200 to all positions over the treatment zone according to the treatment plan and provides 3D EFS of the tumor cells.

Figure 2C:
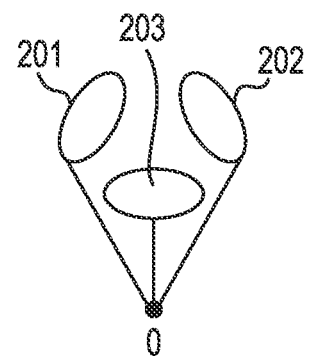
Figure 2B:
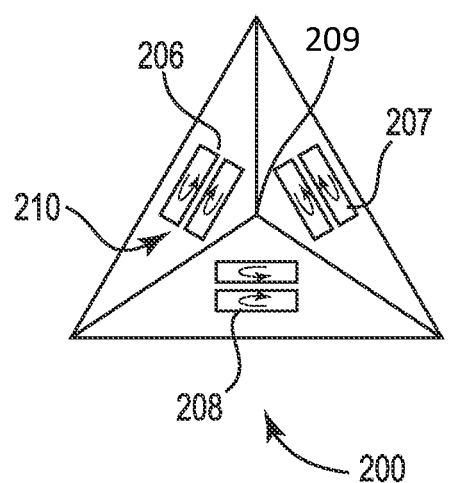

In FIG. 2B the single coils 201, 202 and 203 of FIG. 2A are replaced with double coils 206, 207 and 208 in which the electric currents have opposite directions as shown by arrows in FIG. 2B. In FIG. 2B, coils 206, 207 and 208 are secured on the side planes of a symmetric pyramid with apex 209 and horizontal base 210. The angles between side planes of the pyramid are close to 90 degrees. This coil configuration does not have "dead zones" but provides a lower stimulation field.

Along the axis of a single coil the value of stimulating electric field is zero, whereas the maximum values are reached at a radial distance from the axis approximately equal to the radius of the coil. As schematically shown in FIG. 2C, three straight lines drawn perpendicular to the side planes of the pyramid of FIG. 2A from the lowest parts of the coils cross vertically below stimulator in the point "O", in which the stimulating electric fields reach maxima for all three coils.

Figure 2D:
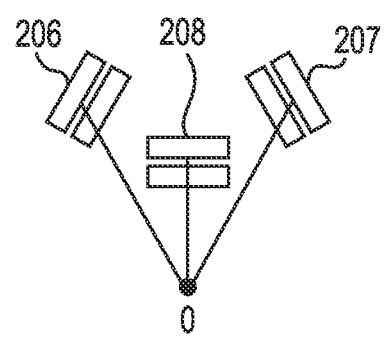

In FIG. 2D similar selection of the point O is schematically shown for the version of stimulator with double coils shown in FIG. 2B. The reference point O for the implementation of the stimulator of FIG. 2B is selected as the crossing of three straight lines drawn perpendicular to the side planes of the pyramid from the centers of double coils, as shown in FIG. 2D.

In a preferred implementation of the invention point O may be selected as a reference point which under control of the computer is being scanned across the patient's tumors delivering EF stimulation. Preprogrammed scanning and dwelling of the maximum EF intensity (point O) by the treatment system 100 provides at least minimum exposure of all parts of the tumor to the EF stimulation.

It should be noted that any higher exposure of some parts of the cancer tumors or healthy tissues during treatment does not produce any detrimental effects: the higher exposure of cancer tissues only increases the probability of cancer cell death, whereas higher exposure of healthy tissues is harmless because healthy tissues are refractory to EF stimulation of intensities used in the disclosed apparatus with and without A3AR agonists in the environment. Only a significant under-exposure of cancer cells to the EFS is unacceptable because such situation allows some cancer cells to avoid full treatment and apoptosis.

Figure 3:
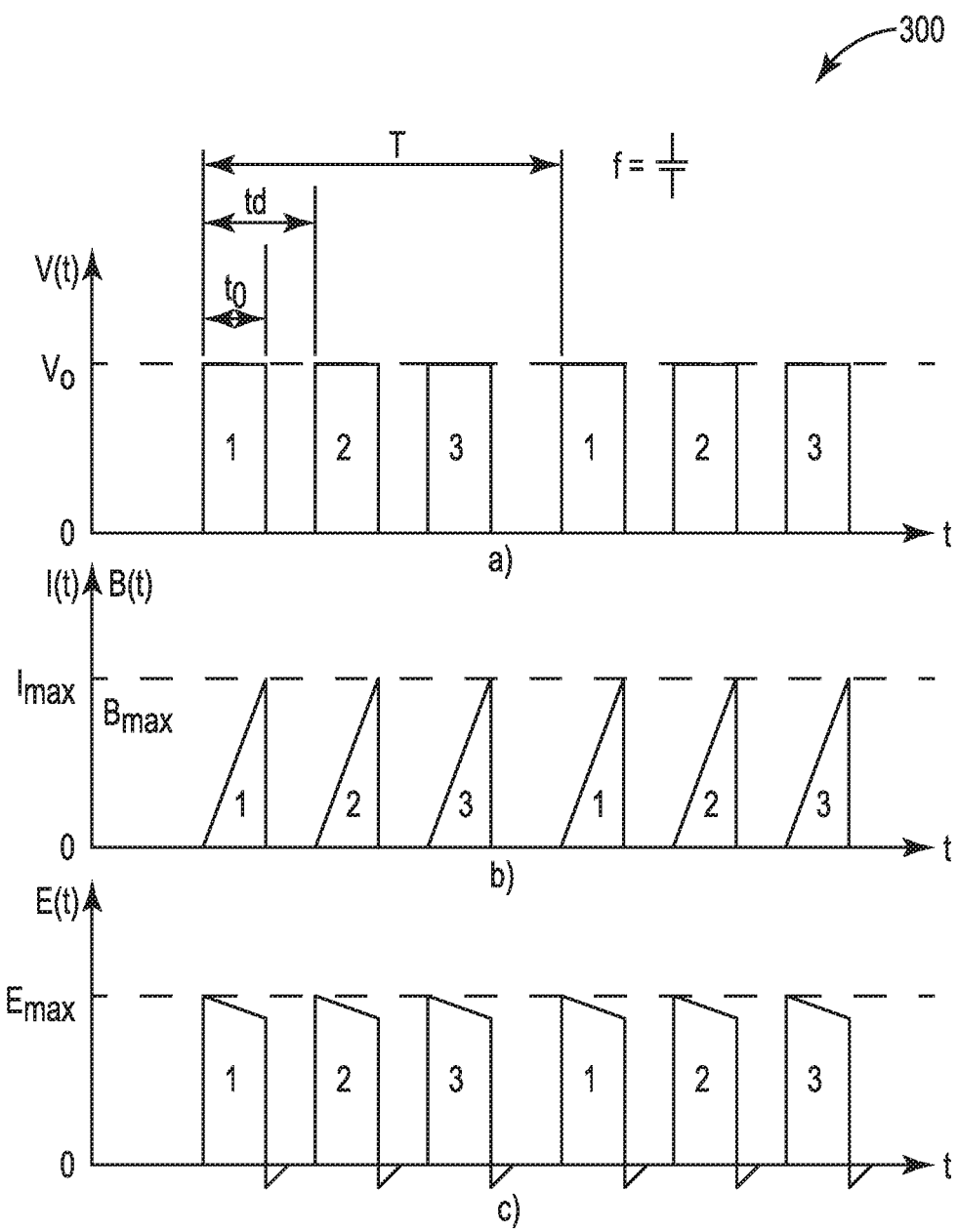
FIG. 3 illustrates the time diagrams of voltage applied to the coils (a), electric current and magnetic field in coils (b) and stimulating electric field in the treatment zone (c).

Diagram a) of FIG. 3 shows a time of voltage applied to the coils. Electronics block 110 supplies the coils of stimulator 108 with a series of rectangular pulses marked 1, 2, and 3. The pulses may have amplitude $V_0$ ranging from 24V to 250V, duration to between 5 μs to 1000 μs and frequency f (f=1/T) from 2 Hz to 250 Hz, where T is the period between two consecutive series of pulses. The pulses in the sequence are delayed by time $t_d$ that is longer than duration of pulses $T_0$, so they do not overlay each other.

Diagram b) of FIG. 3 shows the electric current I(t) and magnetic field B(t) in the coils. An exemplary value of maximum current $I_{max}$ is 200 A to 1000 A and a value of magnetic inductance lies in the range of 4 to 50 milliTesla. The diagram represents ascending exponential curves close in shape to a straight line.

Diagram c) of FIG. 3 depicts the pulsed electric field in the treatment zone with amplitude $E_{max}$ equal to 20-50 mV/cm.

In another implementation of the apparatus, electronics block 110 may supply the coils of stimulator 108 with voltage pulses sequence 1, 1, 1 for several seconds or minutes, then series pulses 2, 2, 2 and series pulses 3, 3, 3.

Figure 4:
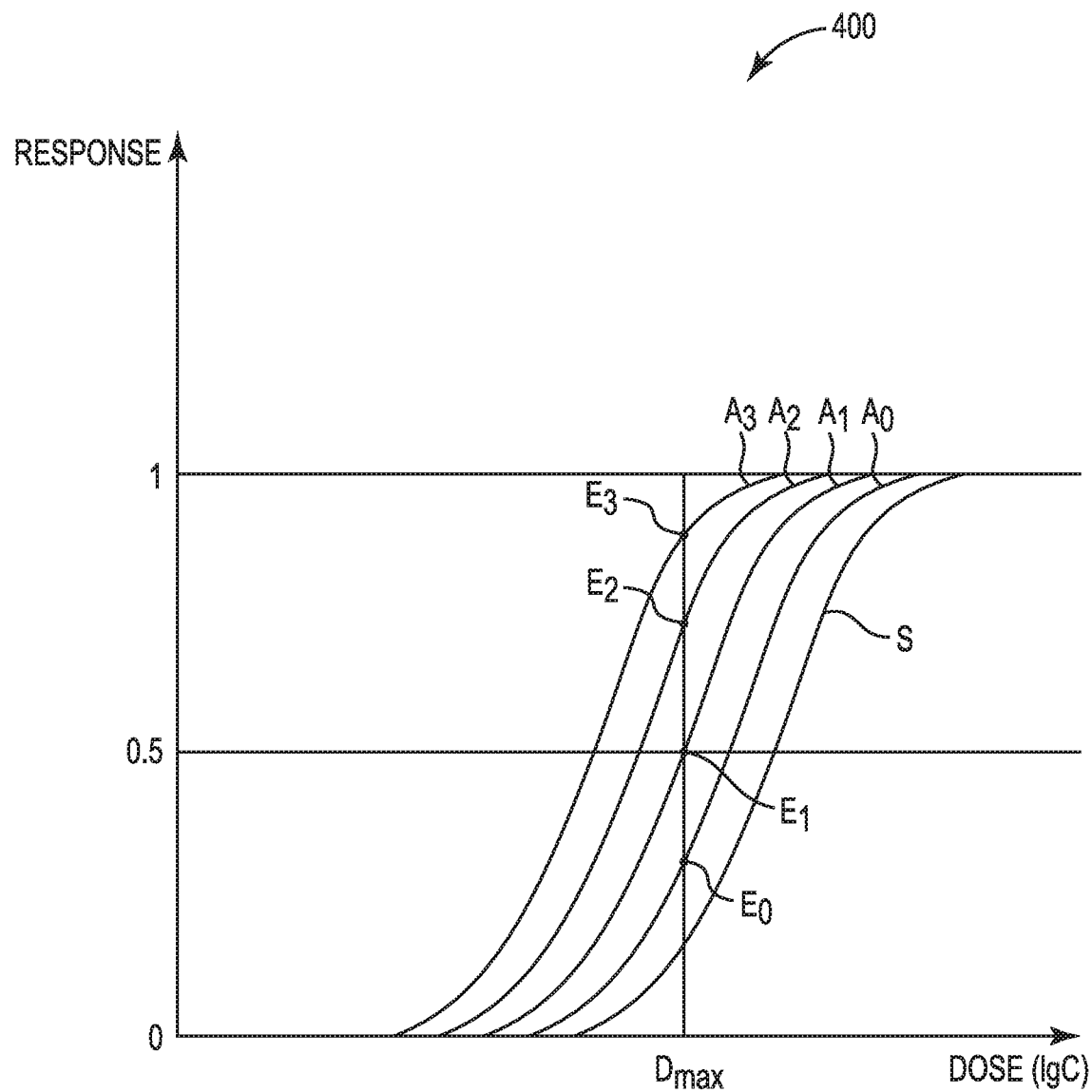
FIG. 4 is a Dose-Response diagram: for adenosine A3AR agonist treatment without EFS (curve A0); with EFS of one dimensional (curve A1), two dimensional (curve A2) and three-dimensional stimulation (curve A3). The diagram also illustrates the effects of simultaneous delivery of A2aAR agonists and EFS for opening the BBB.

In FIG. 4 a dose-response diagram illustrates the effects of cancer treatment with A3AR agonists alone and in combination with EFS. The horizontal axis designates the concentration of A3AR agonist in a logarithmic scale; the vertical axis shows the beneficial cellular response to the actions of a drug, which in context of this disclosure is apoptosis of cancer cells.

Curve S designates side effects as a function of drug concentration; concentration $D_{max}$ labels the maximum tolerated dose at which the treatment is conducted. Known side effects of A3AR agonists are dizziness, vomiting, cardiac rhythm change, etc.

Curve $A_0$ describes response to treatment with A3AR agonist alone. Curve $A_1$ depicts response to one-dimensional EFS, curve $A_2$ to stronger two-dimensional EFS, and curve $A_3$ response to the strongest three-dimensional EFS. As can be seen from the dose-response diagrams in FIG. 4, the EFS shifts the response curve to the left, to lower concentrations and higher responses. The more intense the EFS—the higher the beneficial effect. A modest starting beneficial effect $E_0$ achieved without EFS increases in intensity-dependent manner to $E_1 \rightarrow E_2 \rightarrow E_3$, the last of which is close to the maximum achievable response.

FIG. 4 also illustrates the effects of A2aAR agonists on permeability of BBB. In this case the horizontal axis designates concentration of the A2aAR agonist in logarithmic scale; vertical axis shows the beneficial response which in this case is the permeability of BBB. Again, EF stimulation shifts the response curve to the left, to lower concentrations and higher responses: the more intense EF stimulation—the higher permeability of the BBB.

To be sure that a given cancer is treatable with A3AR agonists, it is implied that before treatment a biopsy is taken from the tumor, and a cellular culture prepared. In the lab the culture is treated with A3AR agonist: if there is apoptosis of cancer cells or the culture produces p53 protein and/or proteins characteristic of WNT pathway which are signs that the cancer cells will respond to A3AR agonist, then the treatment can follow.

A3AR agonist, exemplary, CF101 (molecular weight 510.3 g/mol) is administered to the patient. CF101 is well tolerated in oral doses of 4 mg twice a day over a week period (Van Troostenburg A R et al.), so EF stimulation can be administrated with this dosing regimen. EF stimulation may start simultaneously with drug delivery.

Duration of EF stimulation session is tumor size-dependent and can be 1-2 hours long per session, two sessions a day, seven day per week. Selection of the treatment schedule is at the physician's discretion. Because the drug and EF stimulation will not produce serious side effects, repetitive treatment can last for several weeks.

In case of treatment of brain tumors, the concomitant administration of A2aAR agonist for opening the BBB can be performed simultaneously with A3aAR agonists. For treatment of a brain tumor, A3AR agonist cordycepin is preferred because it has a very small molecular weight (251.24 g/mol) that makes it easier to pass through the BBB. It is noted that A3AR agonist cordycepin is an active ingredient of the fungus *Cordyceps sinensis*, which has been used for thousands of years in traditional Chinese medicine for cancer treatment.

The selective A2aAR agonist Lexiscan is approved by the FDA and successfully used in myocardial perfusion imaging in humans. Lexiscan is a good candidate for combining with EF stimulation for treatment of brain tumors. Lexiscan induces substantial permeation of the BBB, but in doses used for cardiac perfusion, it creates strong, sometimes life-threatening side effects that are related to dilatation of blood vessels in the whole body. Also, Lexiscan has a short half-life of three minutes, which for cancer treatment that lasts one hour or more suggests continuous IV infusion instead of bolus. Continuous infusion of Lexiscan in low, well tolerated doses in combination with EF stimulation of the tumor site provides a strong and long-lasting increase in permeability of the BBB without significant side effects.

Importantly, this technique could be used for CNS delivery of macromolecular therapeutics like antibodies, which traditionally have been limited in their use for treating neurological diseases. Using A2aAR agonists for opening the BBB is not limited to cancer treatment but can be utilized for drug delivery for any CNS disease.

Adenosine is a primordial molecule that performs many vital biological functions in the body. One of them is being a carrier of energy in cells by ATP, ADP and AMP that provide necessary energy for all biochemical reactions in the cellular machinery. One of the adenosine important functions in the intercellular space is that its concentration serves as an indicator of energy spent by cells and is used by the body for controlling the energy balance in tissues. As an example, during inflammation the energy spending in tissues can be as high as 40 times that of the base level. Acting through adenosine-AZAR anti-inflammatory signaling pathway, adenosine decreases energy consumption by slowing down the activity of the immune system, so the tissue consumption of energy remains in the physiological limits.

Dividing cancer cells consume a tremendous amount of energy and create a hypoxic and energy deprived state in tissue. In this case the high concentration of adenosine acts through the adenosine-A3AR anticancer signaling pathway and limits energy consumption in cancerous cells by induction of their apoptosis. This way the cancer cells are killed if their adenosine-A3AR pathway is viable. If the adenosine-A3AR pathway is compromised by mutations, the system of controlling cancer cells proliferation is broken and unchecked cell proliferation proceeds to full scale cancer. In many forms of cancer, the anticancer adenosine-A3AR pathway is disabled only partially and, as has been demonstrated in multiple studies, can be revitalized by administration of A3AR agonists. Regretfully, this leads only to limited improvement: cancer tumor growth is significantly slowed down, but tumors are not completely destroyed and keep growing.

In an aspect of the current invention, additional means, supplemental to the administration of A3AR agonists, is provided to increase the potency of the adenosine-A3AR anticancer pathway by increasing the expression of A3ARs on the surfaces of cancer cells with EF stimulation. EF stimulation causes a several fold increase in expression of A3ARs on the cell's membranes and thus amplifies a downstream signal that induces apoptosis. As the disease progresses the cancer cells naturally increase expression of A3ARs on their membranes demonstrating their "death wish". So, EF stimulation assists the natural attempts of the body to increase the efficiency of adenosine-A3AR pathway and defeat the cancer.

From a pharmacological point of view, PEMF stimulation in association with administration of A3AR agonists and A2aAR agonists/antagonists is a highly potent and efficient noninvasive and side effects free form of cancer therapy.

It is also within the scope of the invention to combine features, functions, advantages and aspects of the various embodiments described herein. Thus, the embodiments of the invention may comprise combinations of aspects of any one or more of these exemplary embodiments.

While the invention has been described in connection with what is presently considered to be the most practical and preferred example embodiments, it will be apparent to those of ordinary skill in the art that the invention is not to be limited to the disclosed example embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products.

For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:

1. A pulsed electric field stimulation (EFS) apparatus for treatment of cancer, the apparatus comprising:
   an applicator, comprising:
   a first coil provided to the applicator in a first plane;
   a second coil provided to the applicator in a second plane; and
   a third coil provided to the applicator in a third plane, wherein each of the first, second and third planes are mutually orthogonal to one another and arranged in the applicator such that a straight line drawn perpendicular from each coil defines an intersection of the lines vertically below the applicator at a point where a stimulating electrical field for each of the first, second and third coils is at a maximum value.

2. The apparatus of claim 1, further comprising a first actuator coupled to the applicator to articulate the applicator in a first axis.

3. The apparatus of claim 2, further comprising a second actuator coupled to the applicator to articulate the applicator in a second axis, wherein the second axis is perpendicular to the first axis.

4. The apparatus of claim 3, further comprising a third actuator coupled to the applicator to articulate the applicator in a rotational axis.

5. The apparatus of claim 1, further comprising an actuator coupled to the applicator to articulate the applicator in a rotational axis.

6. The apparatus of claim 1 further comprising a computer coupled to the applicator and configured to control movement of the applicator during a treatment regimen.

7. The apparatus of claim 1 further comprising a computer coupled to the applicator and configured to energize each of the first, second and third coils of the applicator during a treatment regimen.

* * * * *